(12) United States Patent
Meissner et al.

(10) Patent No.: US 9,686,969 B2
(45) Date of Patent: Jun. 27, 2017

(54) SELECTIVE EMBRYONIC STRUCTURE TARGETING AND SUBSTANCE DELIVERY DEVICE

(71) Applicants: Merial, Inc., Duluth, GA (US); Agri Advanced Technologies GmbH, Visbek (DE)

(72) Inventors: Sven Meissner, Brand-Erbisdorf (DE); Stefan Geissler, Dresden (DE); Toni Frohnert, Dresden (DE); Doreen Goehler, Dresden (DE); Bjoern Fischer, Limbach-Oberfrohna (DE)

(73) Assignees: MERIAL INC., Duluth, GA (US); Agri Advanced Technologies GmbH, Visbek (DE)

( * ) Notice: Subject to any disclaimer, the term of this patent is extended or adjusted under 35 U.S.C. 154(b) by 190 days.

(21) Appl. No.: 14/517,184

(22) Filed: Oct. 17, 2014

(65) Prior Publication Data

US 2015/0136030 A1   May 21, 2015

Related U.S. Application Data

(60) Provisional application No. 61/891,915, filed on Oct. 17, 2013.

(51) Int. Cl.
| | |
|---|---|
| *A01K 45/00* | (2006.01) |
| *A01K 43/00* | (2006.01) |
| *A01K 43/04* | (2006.01) |
| *G01B 11/00* | (2006.01) |
| *G01N 33/08* | (2006.01) |
| *G02B 3/00* | (2006.01) |

(52) U.S. Cl.
CPC ............ *A01K 45/007* (2013.01); *A01K 43/00* (2013.01); *A01K 43/04* (2013.01); *A01K 45/00* (2013.01); *G01B 11/002* (2013.01); *G01N 33/085* (2013.01); *G02B 3/0081* (2013.01)

(58) Field of Classification Search
CPC ...... A01K 43/00; A01K 45/00; A01K 45/007; A01K 43/04; G01N 33/08; G01N 33/085; G01B 11/002; G02B 3/0081
USPC ........................................................ 119/6.8
See application file for complete search history.

(56) References Cited

U.S. PATENT DOCUMENTS 3,637,249 A * 1/1972 Kuhl ...................... A01K 43/00
                                                                    294/184
4,681,063 A   7/1987 Hebrank
(Continued)

FOREIGN PATENT DOCUMENTS

| DE | 202009015426 U1 | 2/2010 |
| DE | 102009052976 B3 | 12/2010 |

*Primary Examiner* — Daniel J Troy
*Assistant Examiner* — Hiwot Tefera
(74) *Attorney, Agent, or Firm* — Judy Jarecki-Black; Merial Inc.; Chad Kitchen

(57) ABSTRACT

The present disclosure relates to a device for delivering substances to specific embryonic structures, including heart and blood vessels, within a developing avian egg. The disclosure also relates to methods of using the device to produce enhanced avian embryos. Methods include administering to chicken embryos various substances, including vaccines, nutrients, and stem cells. Chickens resulting from enhanced avian embryos have advantages, including greater growth potential and resistance to pathogen infection/infestation.

23 Claims, 13 Drawing Sheets

(56) References Cited

U.S. PATENT DOCUMENTS

| | | | |
|---|---|---|---|
| 4,903,635 A * | 2/1990 | Hebrank | A01K 43/10 119/6.8 |
| 5,784,992 A | 7/1998 | Petitte et al. | |
| 6,176,199 B1 | 1/2001 | Gore et al. | |
| 6,240,877 B1 * | 6/2001 | Bounds | A01K 45/007 119/6.8 |
| 6,244,214 B1 | 6/2001 | Hebrank | |
| 6,286,455 B1 | 9/2001 | Williams | |
| 6,395,961 B1 | 5/2002 | Petitte et al. | |
| 6,741,876 B1 * | 5/2004 | Scecina | A61B 5/14532 600/316 |
| 7,878,147 B2 * | 2/2011 | Correa | A01K 45/007 119/6.8 |
| 8,336,491 B2 | 12/2012 | Yvin et al. | |
| 9,131,666 B2 * | 9/2015 | Yamamoto | A01K 43/00 |
| 2002/0023591 A1 | 2/2002 | Bounds, Jr. | |
| 2003/0056729 A1 | 3/2003 | Correa et al. | |
| 2003/0172392 A1 | 9/2003 | Mendu et al. | |
| 2004/0107912 A1 * | 6/2004 | Hebrank | A01K 45/007 119/6.8 |
| 2005/0263079 A1 * | 12/2005 | Karaca | A01K 45/007 119/6.8 |
| 2006/0075973 A1 | 4/2006 | Wolfe et al. | |
| 2006/0156989 A1 * | 7/2006 | Hebrank | A01K 45/007 119/6.8 |
| 2007/0098733 A1 * | 5/2007 | Emery | A01K 45/007 424/184.1 |
| 2007/0215050 A1 * | 9/2007 | Hebrank | A01K 45/007 119/6.8 |
| 2007/0243199 A1 | 10/2007 | Doelling et al. | |
| 2007/0243212 A1 | 10/2007 | Doelling et al. | |
| 2008/0289578 A1 * | 11/2008 | Rybarczyk, Jr. | A01K 45/007 119/6.8 |
| 2009/0091744 A1 * | 4/2009 | Lawrence | A01K 43/00 356/53 |
| 2010/0307419 A1 | 12/2010 | Nadreau et al. | |
| 2012/0222621 A1 * | 9/2012 | Correa | A01K 45/007 119/6.8 |
| 2013/0213303 A1 | 8/2013 | Comte et al. | |

\* cited by examiner

SELECTIVE EMBRYONIC STRUCTURE TARGETING AND SUBSTANCE DELIVERY DEVICE

INCORPORATION BY REFERENCE

This application claims priority to U.S. provisional patent application No. U.S. Ser. No. 61/891,915, which was filed on Oct. 17, 2013, and which is herein incorporated by reference in its entirety. Moreover, the disclosures of all references cited herein are herein incorporated by reference in their entirety.

FIELD OF THE INVENTION

The present invention relates to a device for delivering substances to specific embryonic structures, including heart and blood vessels, within a developing avian egg. The invention also relates to methods of using said device.

BACKGROUND OF THE INVENTION

Candling and in ovo injection devices and techniques are well known in the art. For example, injection devices are known that inject treatment substances, such as vaccines, antibiotics or vitamins, directly into eggs, in order to limit the mortality rate or increase embryo growth. Such devices conventionally comprise an injection head which comprises a plurality of vertically moveable injectors above a routing conveyor of eggs to be treated, the eggs being conventionally positioned in cells of incubation trays. However, prior to the instant disclosure, no group has disclosed the automated delivery of substances to specific structures or regions of a developing avian embryo.

REFERENCE/LITERATURE/PATENT REVIEW

FR 2 873 894 (to Breuil) proposes an injection head wherein each injector is equipped with its own movement system to move the injector from a raised position to an injection position wherein its needle can inject a substance into the egg.

U.S. Pat. No. 8,336,491 (to Ceva Sante Animale) proposes an alternative solution to selectively injecting fertilized and live eggs, and particularly to inject a substance only in cells containing an egg. Although this approach is more selective than that taught by the Breuil prior art, Ceva fails to disclose or suggest any way to deliver substance to specific parts of the developing avian embryo.

WO 2012016870 (to Ceva Sante Animale) discloses a method for positioning the tip of an injecting or sampling needle, in an avian egg, by comparing measured and reference electrical parameters. The needle is moved until the measured parameters are characteristic of a desired injection and/or sampling target zone. In contrast, the instant disclosure provides devices and methods for acquiring and storing visual information, and subsequently targeting structural locations in a developing avian embryo.

WO 2007126816 (to Embrex) teaches direct injection into the avian embryo body, during the final quarter of incubation, an effective immunizing dose of a immunogenic composition. The application instructs that exemplary muscle tissues are located near the eggshell, and thus are relatively easily reached by injection apparatus without damage to other, embryonic structures. Thus, in contrast to the instant disclosure, the Embrex application expressly warns that penetrating embryonic structures (aside from $4^{th}$ quarter embryo skeletal muscle) is likely to damage the developing embryo.

U.S. Pat. No. 6,244,214 (to Embrex) teaches a "smart probe" apparatus for identifying a specific structure and or compartment within an egg that is in contact with a needle that has penetrated the shell of the egg, and methods for employing the apparatus for delivering compositions into specific structures and/or compartments within an egg. Unlike the instant disclosure, which determines positional information in part by the non-invasive use of transmitted light, the Embrex patent teaches a detector for determining positional information, wherein the detector enters the egg via an opening previously created therein.

EP 2319653 A1 (to Laservorm Gmbh) teaches that egg shells can be cut with directed laser beams, but does not teach or suggest an automated system for injecting substances into specific avian embryonic structures.

Jochemsen & Jeurissen (2002) teach injection of avian eggs as early as Day 16 post-fertilization, but not injection of specific embryonic structures, and certainly not injection prior to 120 hours post-fertilization.

Thus prior to the instant disclosure, no automated embryonic structure targeting injection system was made or disclosed. Accordingly, the present invention is directed a novel injection system, which is capable of automatically, safely, and effectively delivering substances to developing avian embryos.

SUMMARY OF THE INVENTION

It is an object of the present invention to provide a novel, inventive, and useful system for injecting a substance into a specific location within a developing avian embryo, or a specific location within the egg containing the avian embryo. The system ideally comprises 1) a means for aseptically opening the eggs; 2) a means for detecting the location of the embryos; 3) a means for acquiring and storing embryo and device position information; 4) a means for targeting and moving a needle into position for injecting the substance into the specific location; and 5) a means for aseptically closing/sealing the eggs, to allow the embryos to continue develop and ultimately hatch.

The invention also encompasses methods of using the system for aseptically introducing injectable materials, including liquid cell preparations, into developing avian embryos.

These and other embodiments are disclosed or will be obvious from and encompassed by, the following Detailed Description.

BRIEF DESCRIPTION OF THE DRAWINGS

The following Detailed Description, given to describe the invention by way of example, but not intended to limit the invention to specific embodiments described, may be understood in conjunction with the accompanying Figures, incorporated herein by reference, in which.

DETAILED DESCRIPTION

Figure 1:
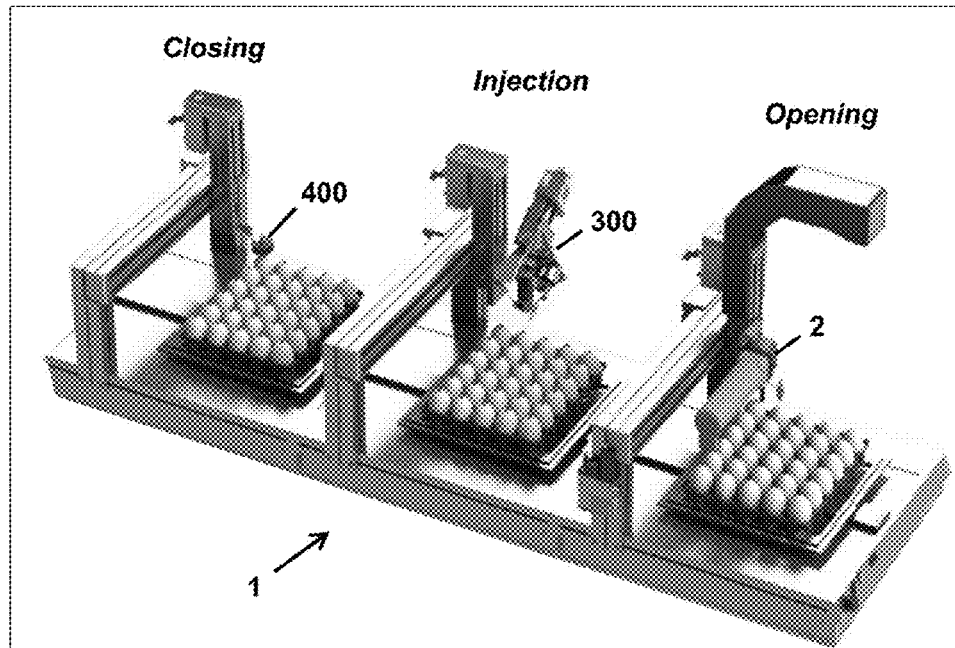
FIG. 1 depicts a laboratory scale embodiment of the injection system (1) according to the disclosure. The system functions by first opening a plurality of eggs using an opening means (2), injecting the eggs using an injection targeting system (300), and finally, aseptically sealing the eggs using an egg-closing means (400)
Figure 2A:
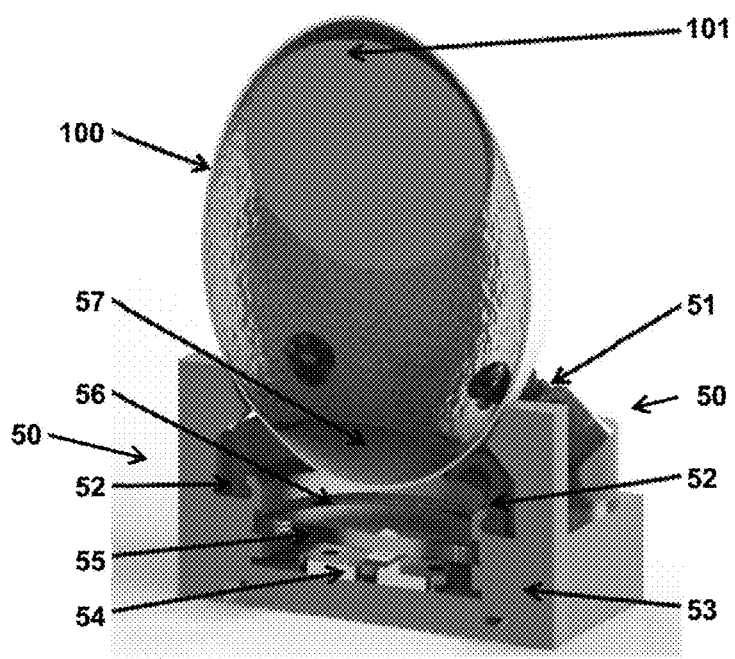
FIG. 2A depicts a cross section of an egg-retaining and illumination means (50) of the injection system. Each egg-retaining means comprises: a negative pressure/vacuum cup (51); a blanket (52); a cooling base (53); a light source (54); safety glass (55); and a positive pressure chamber (56). When an egg is present on the egg-retaining means (50), an air cavity (57) is formed. Throughout the disclosure, eggs will be indicated in the Figures by (100), and embryos will be indicated by (101)
Figure 2B:
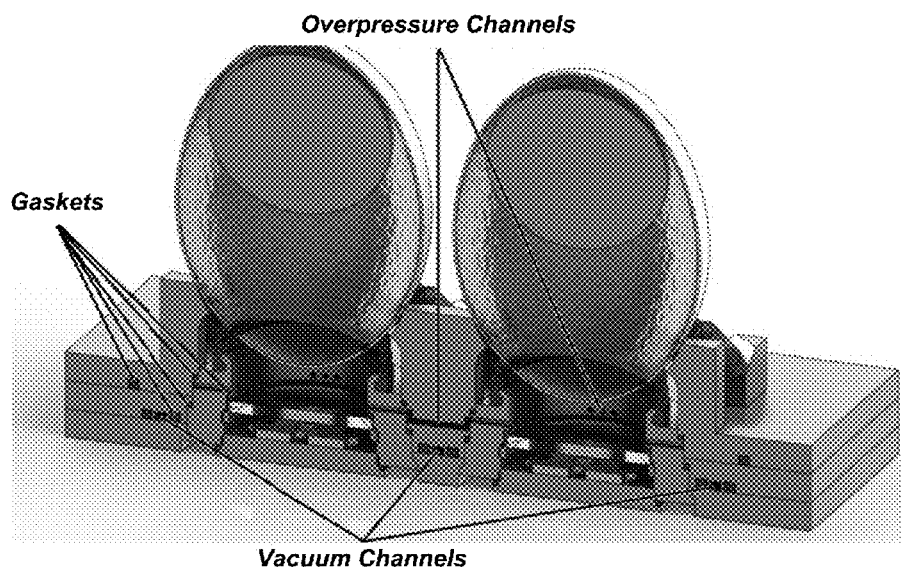
FIG. 2B depicts two consecutive egg-retaining and illumination means (50)
Figure 2C:
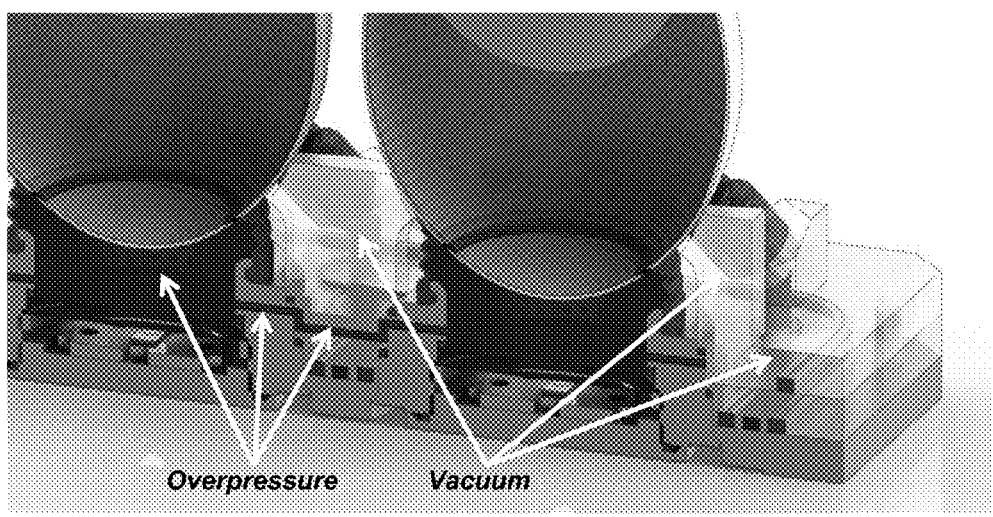
FIG. 2C depicts two consecutive egg-retaining and illumination means (50), rendered transparently, to show regions held above (overpressure) and below (vacuum) ambient pressure.
Figure 3:
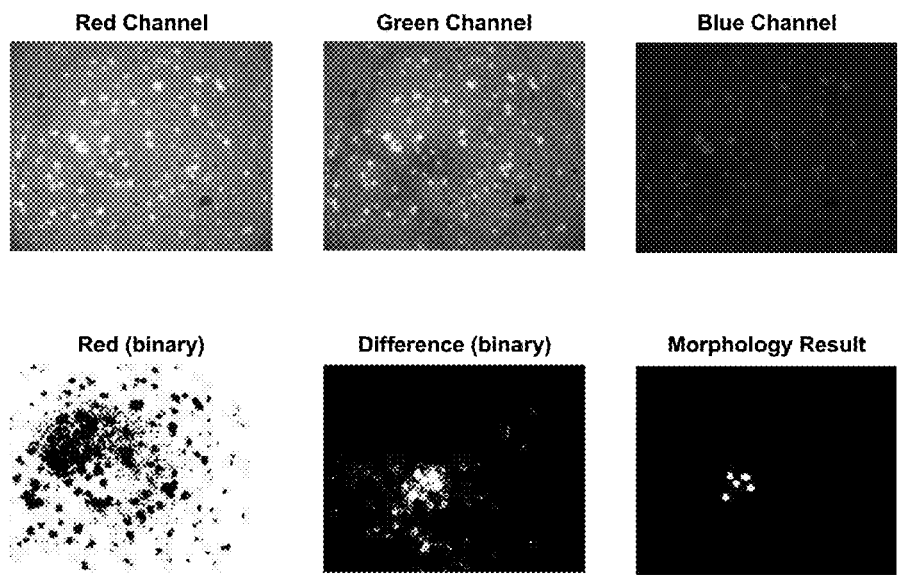
FIG. 3 shows representative images obtained using the image capture functionality of an injection system according to the disclosure.
Figure 4:
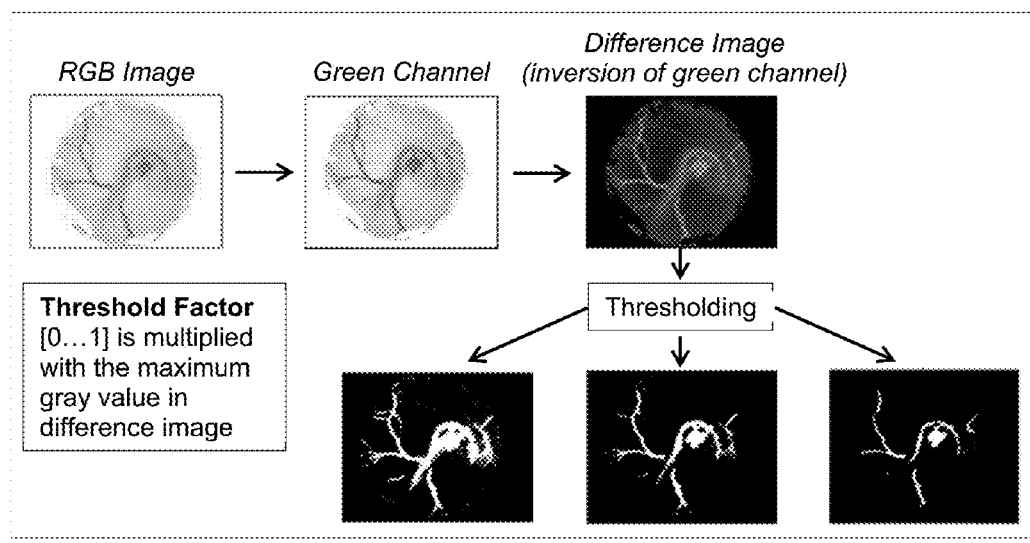
FIG. 4 illustrates the how the images are processed to detect the location of the embryo.

In a first object, the instant disclosure provides an Embryonic Structure Targeting Injection System (hereinafter "ESTIS" or "the System") for injecting a substance into a specific location within a developing avian embryo, or a specific location within the egg containing the embryo.

In an embodiment of the first object, the ESTIS comprises a means for aseptically cutting the outer shell of an egg, such that a defined portion of the shell is prepared for subsequent removal. The ESTIS may further comprise: a means for removing the defined shell portion to produce an opening in the egg; a means for mapping (or targeting) the x, y, z coordinates of embryonic structures to locate the desired specific injection location; a means for injecting the specific substance into the specific injection location; a means for aseptically sealing the opening; combinations of any of the proceeding means; or all of the proceeding means.

Thus in a particular embodiment, the apparatus comprises: a means for aseptically cutting the outer shell of an egg, such that a defined portion of the shell is prepared for subsequent removal. The ESTIS may further comprise: a means for removing the defined shell portion to produce an opening in the egg; a means for mapping (or targeting) the x, y, z coordinates of embryonic structures to locate the desired specific injection location; a means for injecting the specific substance into the specific injection location; and, a means for aseptically sealing the opening.

In an embodiment, the apparatus comprises an egg transfer assembly, which is capable of moving eggs from their incubation position (stump pole facing upward) to their injection position (pointed pole facing upward, accessible to the injection needle).

In another embodiment, the apparatus comprises an egg holder or tray comprising: an egg immobilization means, which employs either vacuum or a suitable mechanical means to fix the position of the egg or plurality of eggs; and a light source, or plurality of light sources, which is a component of the mapping means.

In an embodiment, the holder or tray is disinfectable, bio-compatible, and compatible with standard hatchery trays.

In an embodiment, the apparatus comprises a pressure application means, which serves to apply a positive pressure to the air cavity in the stump end of the egg to diminish embryo deepening (repositioning) after opening of the egg.

In an embodiment, the apparatus the apparatus comprises a cooling means for cooling the light source or plurality of light sources.

In an embodiment, the light source is selected from white light and a specific color of light, wherein the specific color of light can optionally be produced using optical filters in combination with the white light source.

In an embodiment, the apparatus is used to deliver by injection a specific amount of fluid into the specific location of the avian embryo or egg before 120 hours post-fertilization; and wherein the egg is incubated until the chicken hatches.

In an embodiment, the means for cutting is a $CO_2$ laser, a high-power LED laser, or a mechanical cutting means. The mechanical cutting means may be, for example, a diamond or carbide drill.

In an embodiment, the means for mapping the x, y, z coordinates comprises a camera and a microprocessor.

In an embodiment, the LED light is green (center wavelength 535 nm, range 520 nm-550 nm); blue (center wave length 450 nm, range 440 nm-470 nm); yellow (center wave length 590 nm, range 575 nm-610 nm); or NIR (center wave 1200 nm, range of 1000 nm-1400 nm). In a particular embodiment, the LED light is green.

In another embodiment, the injection location is a blood vessel or the heart. In a particular embodiment, the location is the heart and the volume of the delivered/injected substance is 5 µL.

In a second object, the instant disclosure provides a method for safely injecting a substance into a specific location of an avian embryo, or the egg containing the embryo, comprising the steps of:
 a. opening a fertilized avian egg;
 b. injecting a substance into a specific location of embryo or egg; and
 c. sealing the opening in the egg shell, thereby safely injecting the substance into the specific location of the avian embryo or egg.

In a particular embodiment of the second object, the method is performed using the embryonic structure targeting injection (ESTIS) apparatus as disclosed above.

In an embodiment, the method comprises the steps of:
 a. detecting and locating the embryo and its structures without physically disrupting the egg's shell;
 b. penetrating the egg shell, but not the egg membrane, such that a defined portion of said egg shell is capable of being removed by a subsequent removal step; and
 c. removing the defined egg shell portion, leaving behind the opening in said egg shell.

In another embodiment, the method comprises the steps of:
 a. detecting the x and y coordinates for the embryo and its structures;
 b. detecting the z coordinate, which represents the distance between the cutting means and the egg shell surface;
 c. determining a desired target structure, defined by x and y coordinates, into which a substance will be injected;
 d. positioning an injection needle tip sufficiently close to the determined target to allow for injection into the desired target embryonic structure; and
 e. injecting the substance into the structure.

In an embodiment, the method comprises the steps of:
 a. detecting and locating the embryo and its structures without physically disrupting the egg's shell by:
  i. detecting the x and y coordinates for the embryo and its structures;
  ii. detecting the z coordinate, which represents the distance between the opening means and the surface of the egg shell;
  iii. determining a desired target structure, defined by x, y, and z coordinates, into which a substance will be injected;
 b. penetrating the egg shell such that a defined portion of said egg shell is capable of being removed by a subsequent removal step; and
 c. removing the defined egg shell portion, leaving behind the opening in said egg shell;
 d. positioning an injection needle tip sufficiently close to the determined target structure to allow for injection into the desired target structure; and
 e. injecting the substance into the structure.

In an embodiment, the method comprises the steps of rotating the egg, or plurality of eggs, from its incubation position, wherein the egg's stump pole is facing upward, to an injection position, wherein the egg's pointed pole is facing upward such that it is accessible to the injection needle.

In an embodiment, the rotation is accomplished using a vacuum cup assembly.

In another embodiment, the egg or plurality of eggs is placed on an egg holder or tray, which holder or tray comprises:

a. an egg immobilization means which employs either vacuum or a suitable mechanical means to fix the position of the egg or plurality of eggs; and b. a light source or a plurality of light sources.

In an embodiment, the method comprises applying a positive pressure to the air cavity in the stump end of the egg to avoid embryo deepening after opening of the egg.

In another embodiment, the method comprises shining light through the egg, from stump end to pointed end, to a detector unit, which is a component of the mapping means, such that the detection unit is positioned on the opposite side of the egg, relative to the light source. The detection unit may be an area sensor (CMOS or CCD). The detector may be made of silicon or a NIR sensitive material. In and embodiment, the NIR-sensitive material is indium gallium arsenite.

In an embodiment, the detection unit comprises optics including a tunable lens to adjust the focus of the optics to the egg surface. An image may be acquired, digitized, and subsequently transmitted to an image processing unit. In an embodiment, the image processing unit may compute the x and y coordinates of the embryo beneath the egg shell, and deliver the x and y coordinates to the cutting means.

In an embodiment, the surface of the egg shell, or the z coordinate, is detected by a distance sensor, which may be ultrasonic, 1D optical, or 2D laser-triangulation or a 2D or 3D optical coherence tomography sensor; and wherein the detected z coordinate represents the distance between the egg shell and the opening device.

In an embodiment, the cutting means is placed utilizing a 3-axis linear translation stage, a 5-axis linear translation stage, 3-axis portal robot unit, a 5-axis portal robot unit, or a selective compliance assembling robot arm (SCARA); or wherein the egg is moved to a position under a cutting means that remains fixed.

In another embodiment, the opening means comprises an optical device selected from a CO2 laser, a Nd:YAG-laser, an NIR laser, and any laser with a working wave length of from about 1 μm to about 50 μm; or comprises a mechanical device selected from a drill, a hollow drill, a rock drill, a diamond drill, and a carbide drill. The opening means may further comprise a 2D scanner.

In an embodiment, the opening can be made by a punching unit, which punches a hollow tube through the egg shell.

In another embodiment, the opening means cuts the egg shell only, or also cuts the egg shell membrane, and wherein the cutting line is not restricted to any fixed geometric shape, but is instead freely adjustable.

In an embodiment, the removing of the defined portion of the egg shell is accomplished by vacuum suction cup, contact-less vacuum suction, or a mechanical arm. The removing may optionally include removing of a defined portion of the egg shell membrane.

In an embodiment, the detecting of the embryo's x and y coordinates is repeated to acquire and digitize an image of the embryo. The image may be transmitted to a computing unit where image processing software then computes/determines a suitable injection point, defined by x, y and z' coordinates, wherein z' represents the distance between the injection unit and the embryonic structure. In the embodiment, the embryonic structure is selected from a heart, a heart chamber, a vessel, a vein, an artery, and any other structure of the blood vessel system.

In an embodiment, the z' coordinate is determined using optical coherence tomography, ultrasonic measurement, 1D laser triangulation, or 2D Laser triangulation.

In embodiment, the injection point coordinates are delivered to the injection means. In such an embodiment, the tip of an injection needle is positioned at the x, y, and z' coordinates using a 3-axis linear translation stage, a 5-axis linear translation stage, 3-axis portal robot unit, a 5-axis portal robot unit, or a SCARA.

In another embodiment, the egg is moved to the injection needle, such that the tip of the needle is brought into close proximity to the x, y, and z' coordinates. The needle may be positioned between about 0° and about 90° degrees, relative to the injection point coordinates.

Figure 7A:
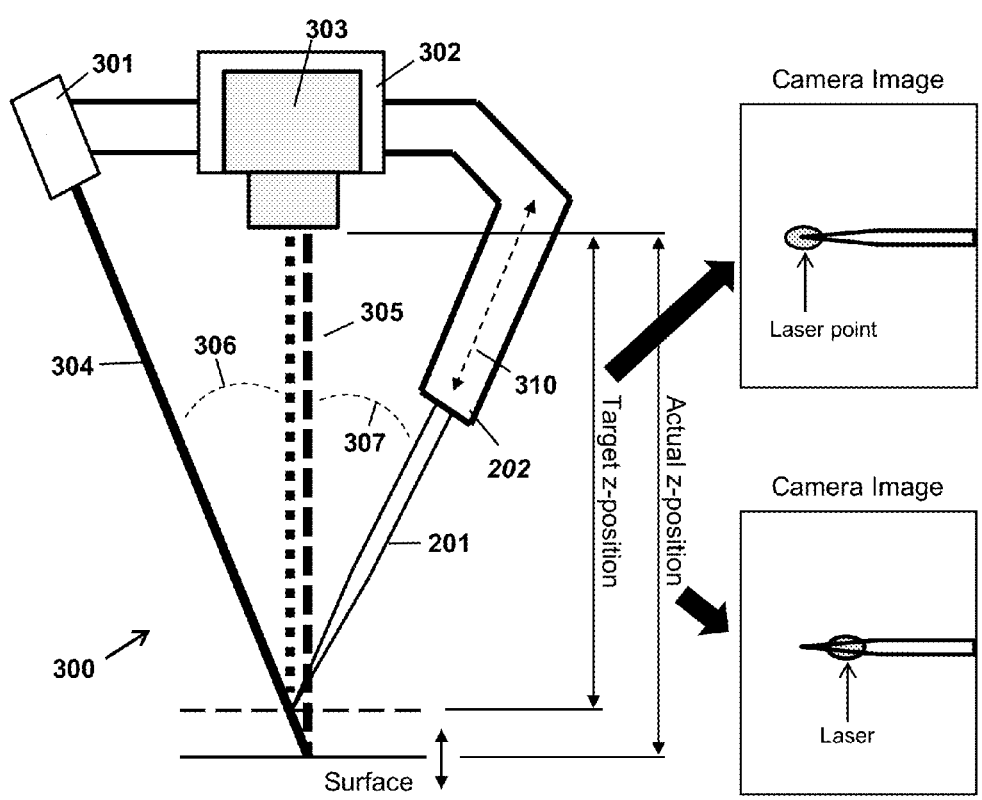
FIG. 7A depicts a configuration of a needle targeting/injection assembly (300) according to the disclosure. The needle (201) is moved until the needle's tip reaches the previously-determined z-position. The targeting assembly is programmed to stop the needle's movement when the camera receives a strong light signal, which is the laser light reflecting off the needle's tip.
Figure 7B:
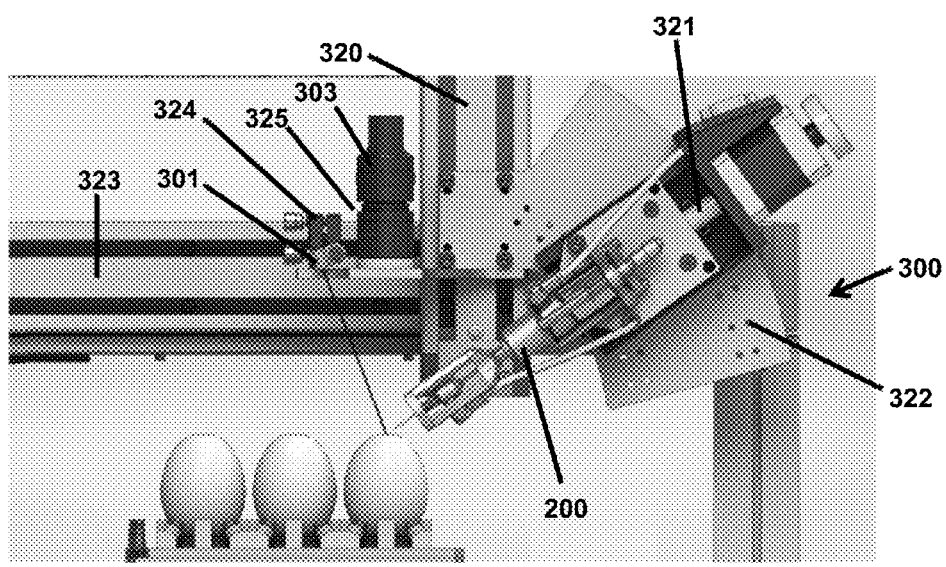
FIG. 7B depicts a particular embodiment of a robotic needle targeting/injection assembly (300). Indicted features are the z-axis (320), the injection axis (321), mounting holes (322), which determine the injection angle for the injection unit (200), the y-axis (323), the laser (301), the laser beam adjustment means (324), the camera optics (325), and the camera (303)
Figure 7C:
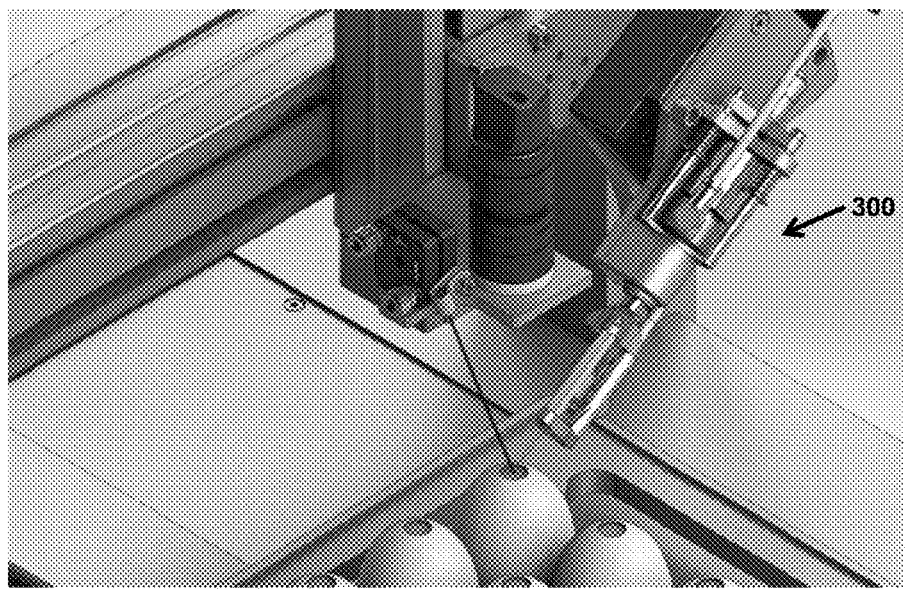
FIG. 7C depicts another view of the assembly (300)
Figure 8:
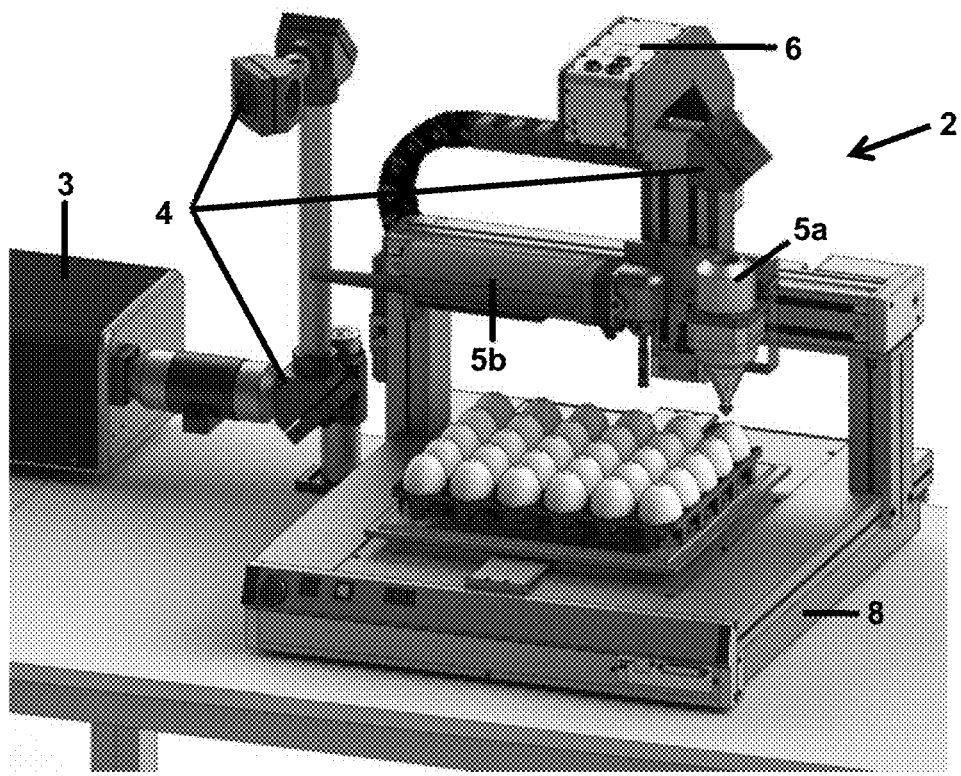
FIG. 8 depicts an embodiment of the opening means (2) equipped with either a cutting laser head (5a), or an alternative drill (5b) opening means. Indicated also are a laser source (3), mirrors (4) for directly the laser light to the laser head (5a), a laser triangulation scanner (6), and a portal robot (8) for moving the various components to achieve opening of the eggs.

In an embodiment, the needle is positioned by a targeting system (300), substantially as depicted in FIG. 7A or 7B. Prior to detecting the embryo, the "x" position of the needle is determined and its value stored. The "y" position is fixed. When the needle is hit by the targeting laser (301), the camera (303) detects the reflected light. The geometry and known angles (i.e. between laser/camera and laser/needle) allow for the subsequent calculation of the needle tip's "z" position. After the needle's x position has been stored, the x and y positions of the target (embryo vessel or heart) are detected using the video camera (values also stored). Next, the egg and/or targeting system is moved to bring the x and y coordinates of the needle tip over the detected injection point. Finally, the whole setup is moved in the z-direction until the laser beam hits the detected injection point in the camera image. The geometry of the assembly ensures that when the laser beam hits the detected injection point, the needle tip will also hit the detected embryonic structure.

In this particular embodiment, a targeting laser (301) is mounted to a camera holder (302), such that a pre-determined, fixed angle (306) is formed between the path (304) of the laser (301) and the line that is perpendicular to the image capture lens of the camera (303) (i.e. the direction in which the camera is fixedly pointing). The angle between the needle (201) and the camera (303) is also fixed, such that the only directions the needle can move (independently of the camera and the path of the laser) is towards or away from the path of the laser. This needle motion path is represented by the bidirectional, dashed line arrow (310).

Figure 5:
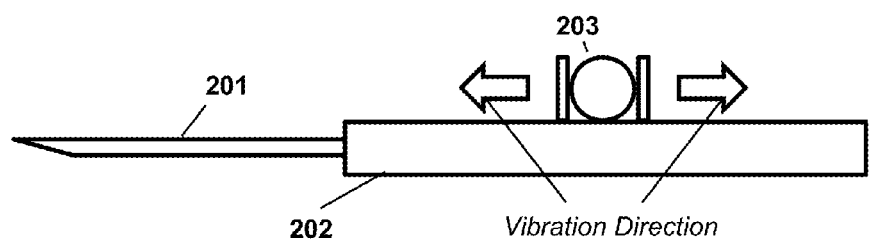
FIG. 5 depicts a needle holder (202) equipped with a vibrating means (203), for moving the needle towards and away from a target z-position.
Figure 6:
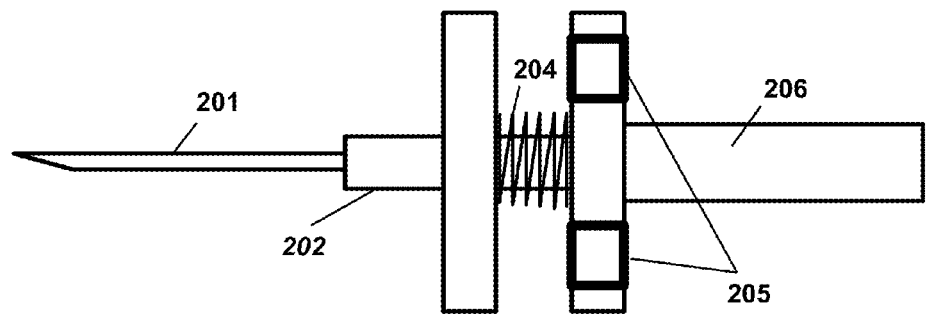
FIG. 6 depicts a needle holder (202) equipped with a spring (204) and electromagnets (205), for moving the needle slidingly within a hollow cylinder (206), towards and away from a target z-position.

In an embodiment, the needle (201) is placed into the embryonic structure using linear motion, oscillating motion, rapid oscillating motion, or a high speed "injection gun" motion. In a particular embodiment, the needle (201) is equipped with a vibration motor, substantially as shown in FIG. 5. Alternatively, the needle may be equipped with electromagnets and a spring, which provides a biasing force, substantially as shown in FIG. 6.

In another embodiment, a substance is injected into the embryonic structure, and the substance is selected from fluid, cells, antibody, vaccine, virus, bacteria, markers, nucleic acids and any other suitable substance.

In an embodiment, the aseptic sealing is accomplished using a membrane, which seals and protects the developing embryo, enabling it to hatch. The membrane may be warmed near to its melting point to allow the membrane to bond to the egg shell. Moreover, the warming may be accomplished using a hot air gun, a flexible stamp filled with circulating hot fluid, a radiation source, an infrared source, or a laser.

Figure 9A:
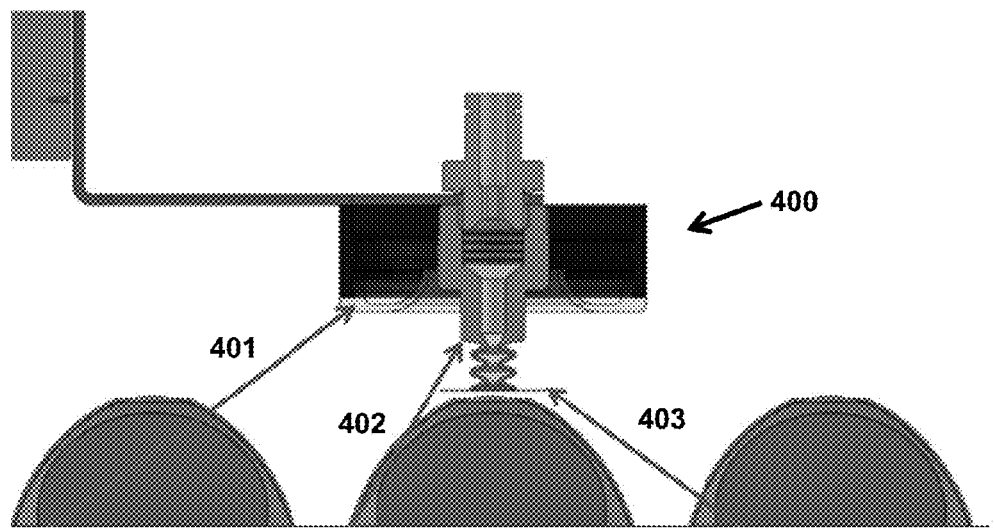
FIG. 9A depicts an egg-closing means (400) according to the disclosure. Shown in this embodiment is a heating unit (401), and a stamping means (402), for applying a sealing material (403), which may be a square of parafilm or any other suitable sealing material.
Figure 9B:
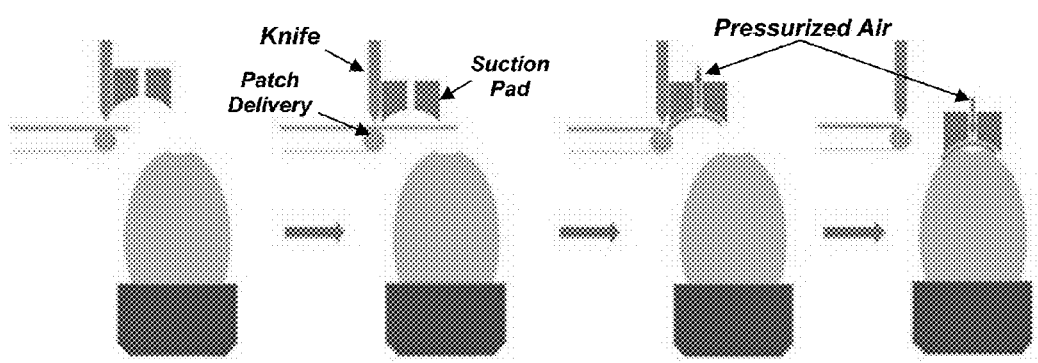
FIG. 9B depicts another embodiment of an egg-closing means (400) according to the disclosure.
Figure 10:
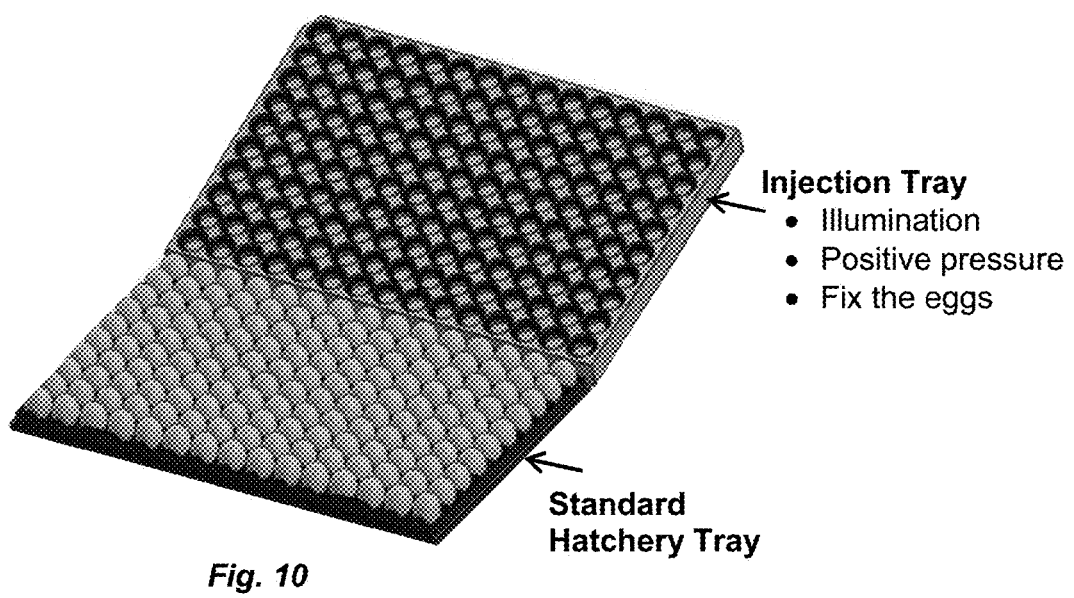
FIG. 10 presents a standard hatchery tray with a corresponding injection tray (20) according to the disclosure. The tray (20) comprises an array of egg-retaining and illuminating means (50), as presented in FIGS. 2A-C.
Figure 11:
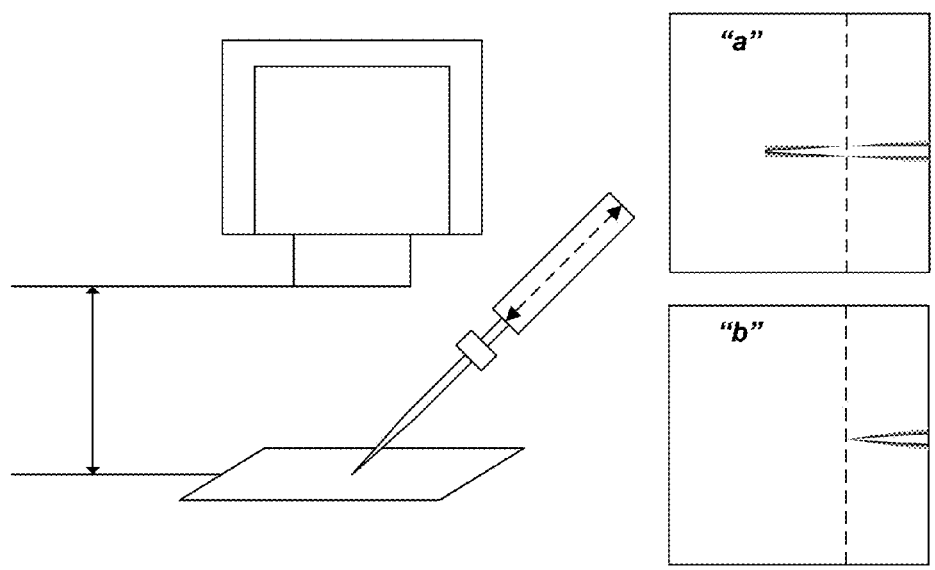
FIG. 11 is a diagram showing "needle detection method 1—static Region of Interest (ROI)." The needle detection methods are performed prior to the injection x and y position detection. In this method, the needle is moved from a first position (a) until the needle tip is positioned in the field of focus of the camera (b). The field of focus is defined manually, before the needle detection.
Figure 12:
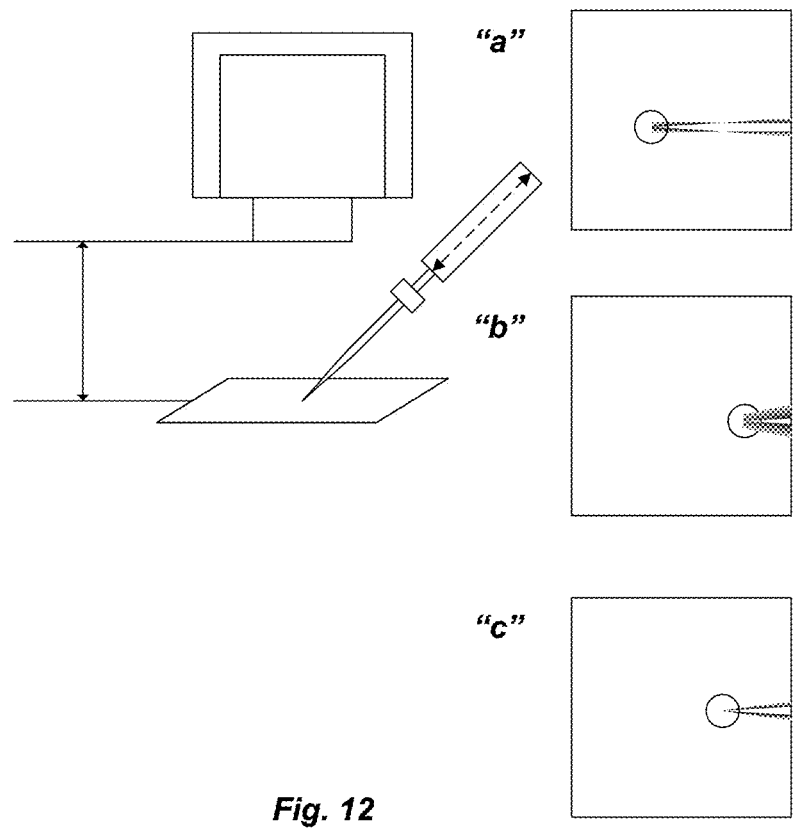
FIG. 12 is a diagram showing "needle detection method 2—dynamic ROI." In this method, the needle is moved through the focus plane of the camera optics. After defined intervals, the needle is stopped, and an image of the needle tip is acquired. After having acquired one image sequence (i.e. the needle passed the focal plane one time), the images were analyzed. The ROI for analysis is always placed in the region of the needle tip, so that the needle tip is definitely within the ROI. For each image, edge detection is carried out. The image with the highest number of detected edges represent the focal plane. (a) below the focal plane; (b) above the focal plane; and (c) in the focal plane. Accordingly, the location of the needle tip in the image in the focal plane (c), is the location of the needle tip.
Figure 13:
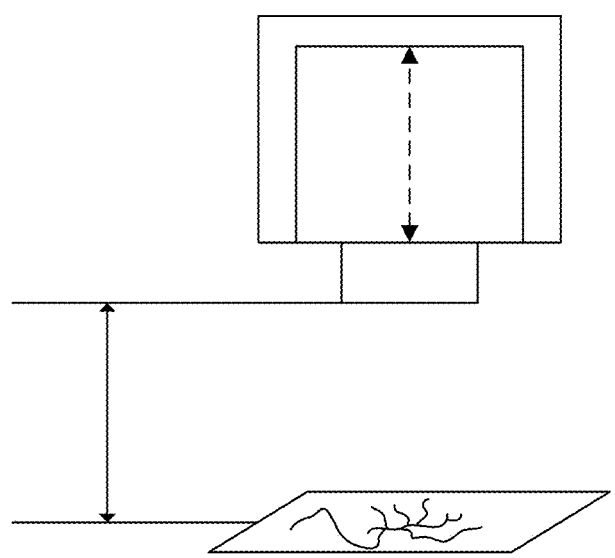
FIG. 13 is a diagram showing how the distance to the target (the "z-position") may be measured. In method 1, the camera is moved up and down while continuously acquiring images until the sharpest image is taken. The detection of the sharpness may be carried out using edge detection as well as measuring the variance within the image. To increase the accuracy of the detected sharpness, a, ROI may be defined within the acquired images.
Figure 14:
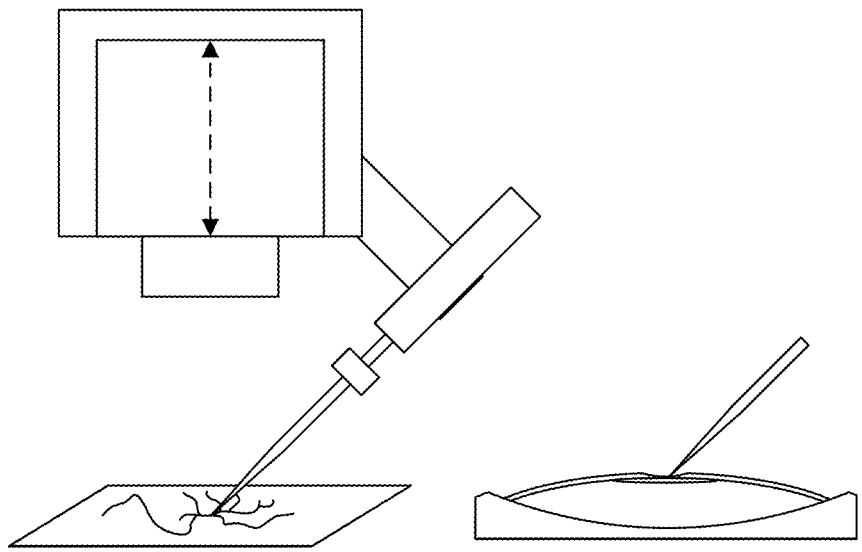
FIG. 14 is a diagram showing a second z-position detection method—distance measurement by contact. After the needle is positioned in the focal plane of the video camera, the distance between the needle and the egg's surface is measured. A light is shone on the egg surface, and the needle is moved forward until it touches the surface of the egg. The precise time the needle reaches the surface may be detected by measuring changes in reflection (i.e. as detected by the continuous capture of images by the video camera). When a change in image intensity (caused by the reflection of the light source) is detected, the needle has reached the surface of the egg.
Figure 15:
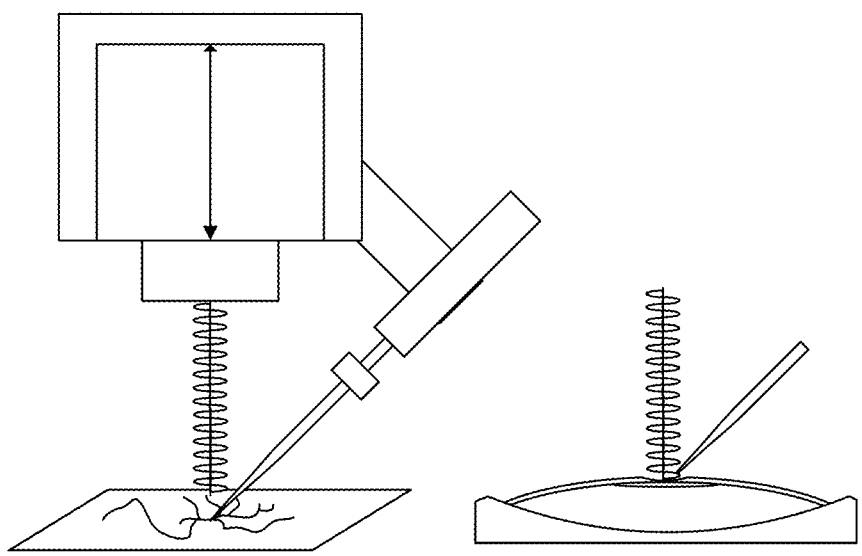
FIG. 15 is a diagram showing a third z-position detection method—distance measurement by optical coherence tomography (OCT). After positing the needle in the focal plane of the video camera, an OCT imaging system is used to measure the z-position. The OCT light is guided by the same optics as is the visible light for the video camera, and continuously acquires a 2D image of the egg's surface. For detection the z position of the egg surface, the camera, along with the needle, is moved down to the egg's surface. The continuously acquired 2D OCT images detect the precise moment the needle touches the egg's surface.
Figure 16:
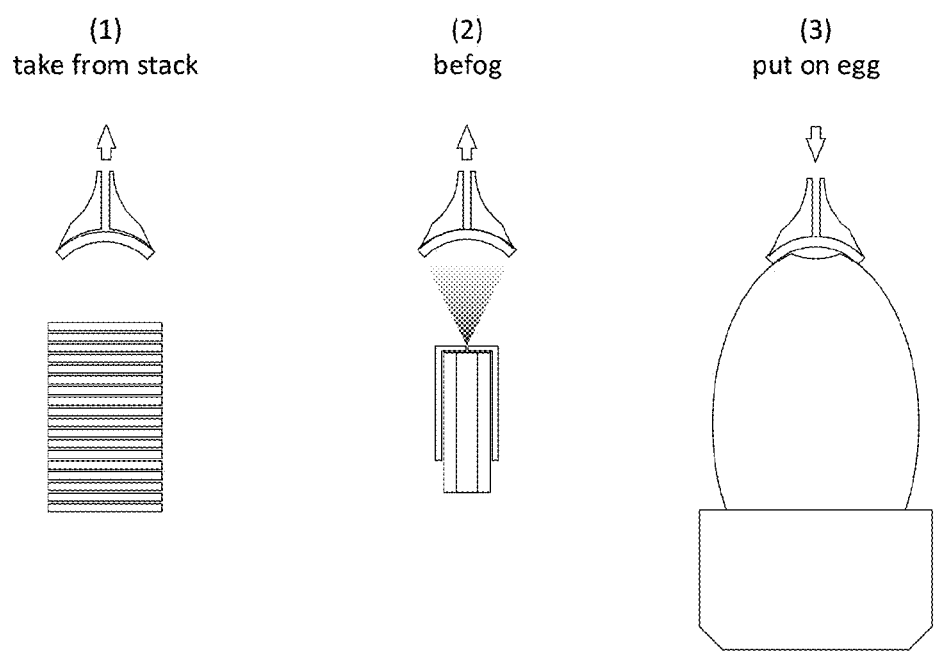
FIG. 16 is a diagram showing an alternate method for closing the eggs. As shown, the holes may be closed utilizing non-adhesive tapes, which can be store in stacks. The advantage of this method is that the glue is placed on the tape immediately before the closing procedure, which minimizes handling of the tape. Non-adhesive tapes may be stored in stacks, without any kind of carrier foil. In this closure method, the tape is first collected by a vacuum suction cup (1); sprinkled with glue/water, in the case of a "wet adhesive tape" (similar to a stamp) (2); and finally, placed over the hole, thereby sealing the egg (3).

In another embodiment, the aseptic sealing is accomplished using a self-adhesive tape. The self-adhesive tape may be placed for sealing as shown in FIG. 9B. The sealing may also be carried out substantially as outlined in FIG. 16.

In such an embodiment, the egg may be sealed using the following steps:

1) using a suction cup to pick up a sealing sheet, from a stack of sealing sheets;
2) spraying the sheet with a liquid, including glue and water; and
3) depositing the wetted sheet onto the egg's opening, thereby sealing the egg.

In a particular embodiment, greater than 1,000 eggs are injected per hour. In an even more particular embodiment, greater than 3,000 eggs are injected per hour.

Each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, nonobvious, inventive, over the prior art, e.g., over documents cited herein or incorporated by reference herein. And, the terms "consists of" and "consisting of" have the meaning ascribed to them in U.S. Patent law; namely, that these terms are closed ended. The singular terms "a", "an", and "the" include plural referents unless context clearly indicates otherwise. Similarly, the word "or" is intended to include "and" unless the context clearly indicates otherwise.

Having thus described in detail embodiments of the present invention, the invention will now be described in the following numbered paragraphs.

1. An Embryonic Structure Targeting Injection System (ESTIS) for injecting a substance into a specific location within a developing avian embryo, or the egg containing the embryo, comprising:
   a. a means for aseptically cutting the outer shell of an egg, such that a defined portion of the shell is prepared for subsequent removal;
   b. a means for removing the defined shell portion to produce an opening in the egg;
   c. a means for mapping (or targeting) the x, y, z coordinates of embryonic structures to locate the desired specific injection location;
   d. a means for injecting the specific substance into the specific injection location; and
   e. a means for aseptically sealing the opening.

2. The apparatus of paragraph 1, further comprising an egg transfer assembly, which is capable of moving eggs from their incubation position (stump pole facing upward) to their injection position (pointed pole facing upward, accessible to the injection needle).

3. The apparatus of paragraph 1, further comprising an egg holder or tray comprising:
   a. an egg immobilization means, which employs either vacuum or a suitable mechanical means to fix the position of the egg or plurality of eggs; and
   b. a light source, or plurality of light sources, which is a component of the mapping means.

4. The apparatus of paragraph 3, wherein the holder or tray is disinfectable, bio-compatible, and compatible with standard hatchery trays.

5. The apparatus of paragraph 3, further comprising a pressure application means, which serves to apply a positive pressure to the air cavity in the stump end of the egg to diminish embryo deepening (repositioning) after opening of the egg.

6. The apparatus of paragraph 3, further comprising a cooling means for cooling the light source or plurality of light sources.

7. The apparatus of paragraph 3, wherein the light source selected from white light and a specific color of light, wherein the specific color of light can optionally be produced using optical filters in combination with the white light source.

8. The apparatus of paragraph 1, wherein a specific amount of fluid is injected into the specific location of the avian embryo, or the specific location of the egg containing the embryo, before 120 hours post-fertilization; and, wherein the egg is incubated until the chicken hatches.

9. The apparatus of paragraph 1, wherein the means for cutting is a CO2 laser, a high-power LED laser, or a mechanical cutting means.

10. The apparatus of paragraph 2, wherein the mechanical cutting means is a diamond or carbide drill.

11. The apparatus of paragraph 3, wherein the means for mapping the x, y, z coordinates comprises a camera and a microprocessor.

12. The apparatus of paragraph 4, wherein the LED light is green (center wavelength 535 nm, range 520 nm-550 nm); blue (center wave length 450 nm, range 440 nm-470 nm); yellow (center wave length 590 nm, range 575 nm-610 nm); or NIR (center wave 1200 nm, range of 1000 nm-1400 nm).

13. The apparatus of paragraph 5, wherein the injection location is a blood vessel or the heart.

14. The apparatus of paragraph 6, wherein the location is the heart and the volume of the substance is 5 µL.

15. A method for safely injecting a substance into a specific location of an avian embryo, or a specific location of an egg containing an avian embryo, comprising the steps of:
   a. opening a fertilized avian egg;
   b. injecting a substance into a specific location of the egg or the embryo; and
   c. sealing the opening in the egg shell, thereby safely injecting the substance into the specific location of the egg or avian embryo.

16. The method of 9 which is performed using the apparatus of paragraph 1.

17. The method of paragraph 9, further comprising the steps of:
   a. detecting and locating the embryo and its structures without physically disrupting the egg's shell;
   b. penetrating the egg shell, but not the egg membrane, such that a defined portion of said egg shell is capable of being removed by a subsequent removal step; and
   c. removing the defined egg shell portion, leaving behind the opening in said egg shell.

18. The method of paragraph 11, comprising the steps of:
a. detecting the x and y coordinates for the embryo and its structures;
b. detecting the z coordinate, which represents the distance between the cutting means and the egg shell surface;
c. determining a desired target structure, defined by x and y coordinates, into which a substance will be injected;
d. positioning an injection needle tip sufficiently close to the determined target to allow for injection into the desired target embryonic structure; and
e. injecting the substance into the structure.

19. The method of paragraph 9, comprising the steps of:
a. detecting and locating the embryo and its structures without physically disrupting the egg's shell by:
   i. detecting the x and y coordinates for the embryo and its structures;
   ii. detecting the z coordinate, which represents the distance between the opening means and the surface of the egg shell;
   iii. determining a desired target structure, defined by x, y, and z coordinates, into which a substance will be injected;
b. penetrating the egg shell such that a defined portion of said egg shell is capable of being removed by a subsequent removal step; and
c. removing the defined egg shell portion, leaving behind the opening in said egg shell;
d. positioning an injection needle tip sufficiently close to the determined target structure to allow for injection into the desired target structure; and
e. injecting the substance into the structure.

20. The method of paragraph 9, further comprising the step of rotating the egg, or plurality of eggs, from its incubation position, wherein the egg's stump pole is facing upward, to an injection position, wherein the egg's pointed pole is facing upward such that it is accessible to the injection needle.

21. The method of paragraph 18, wherein the rotation is accomplished using a vacuum cup assembly.

22. The method of paragraph 18, wherein the egg or plurality of eggs is placed on an egg holder or tray, which holder or tray comprises:
a. an egg immobilization means which employs either vacuum or a suitable mechanical means to fix the position of the egg or plurality of eggs; and
b. a light source or a plurality of light sources.

23. The method of paragraph 22, further comprising applying a positive pressure to the air cavity in the stump end of the egg to avoid embryo deepening after opening of the egg.

24. The method of paragraph 23, wherein the light is shone through the egg, from stump end to pointed end, to a detector unit, which is a component of the mapping means, such that the detection unit is positioned on the opposite side of the egg, relative to the light source.

25. The method of paragraph 24, wherein the detection unit is an area sensor (CMOS or CCD).

26. The method of paragraph 25, wherein detector is made of silicon or a NIR sensitive material.

27. The method of paragraph 26, wherein the NIR-sensitive material is indium gallium arsenite.

28. The method of paragraph 25, wherein the detection unit comprises optics including a tunable lens to adjust the focus of the optics to the egg surface.

29. The method of paragraph 25, wherein an image is acquired and digitized.

30. The method of paragraph 29, wherein the digitized image is transmitted to an image processing unit.

31. The method of paragraph 30, wherein the image processing unit computes the x and y coordinates of the embryo beneath the egg shell, and delivers the x and y coordinates to the cutting means.

32. The method of paragraph 31, wherein the surface of the egg shell, or the z coordinate, is detected by a distance sensor, which is selected from ultrasonic, 1D optical, and 2D laser-triangulation sensors; and, wherein the detected z coordinate represents the distance between the egg shell and the opening device.

33. The method of paragraph 31, wherein the cutting means is placed utilizing a 3-axis linear translation stage, a 5-axis linear translation stage, 3-axis portal robot unit, a 5-axis portal robot unit, or a selective compliance assembling robot arm (SCARA); or, wherein the egg is moved to a position under a cutting means that remains fixed.

34. The method of paragraph 31, wherein the opening means comprises an optical device selected from a CO2 laser, a Nd:YAG-laser, an NIR laser, and any laser with a working wave length of from about 1 μm to about 50 μm; or comprises a mechanical device selected from a drill, a hollow drill, a rock drill, a diamond drill, and a carbide drill.

35. The method of paragraph 34, wherein the opening means, further comprises a 2D scanner.

36. The method of paragraph 31 where the opening can be made by a punching unit, which punches a hollow tube through the egg shell.

37. The method of paragraph 31, wherein the opening means cuts the egg shell only, or also cuts the egg shell membrane, and, wherein the cutting line is not restricted to any fixed geometric shape, but is instead freely adjustable.

38. The method of paragraph 31, wherein the removing of the defined portion of the egg shell is accomplished by vacuum suction cup, contact-less vacuum suction, a mechanical arm; and, wherein the removing optionally includes removing of a defined portion of the egg shell membrane.

39. The method of paragraph 38, wherein the detecting of the embryo x and y coordinates is repeated to acquire and digitize an image of the embryo.

40. The method of paragraph 39, wherein the image is transmitted to a computing unit where image processing software then computes/determines a suitable injection point, defined by x, y and z' coordinates, wherein z' represents the distance between the injection unit and the embryonic structure; and, wherein the embryonic structure is selected from a heart, a heart chamber, a vessel, a vein, an artery, and any other structure of the blood vessel system.

41. The method of paragraph 40, wherein the z' coordinate is determined using optical coherence tomography, ultrasonic measurement, 1D laser triangulation, or 2D Laser triangulation.

42. The method of paragraph 40 or 41, further comprising delivering the injection point coordinates to the injection means.

43. The method of paragraph 42, comprising placing the tip of an injection needle at the x, y, and z' coordinates using a 3-axis linear translation stage, a 5-axis linear translation stage, 3-axis portal robot unit, a 5-axis portal robot unit, or a SCARA.

44. The method of paragraph 42, wherein the egg is moved to an injection needle, such that the tip of the needle is brought to the x, y, and z' coordinates.

45. The method of paragraph 43 or 44, wherein the needle is between about 0° and about 90° degrees, relative to the injection point coordinates.

46. The method of paragraph 44, wherein the needle is placed into the embryonic structure using linear motion, oscillating motion, rapid oscillating motion, or a high speed "injection gun" motion.

47. The method of paragraph 43 or 44, further comprising injecting a substance into the embryonic structure, wherein the substance is selected from fluid, cells, antibody, vaccine, virus, bacteria, markers, nucleic acids and any other suitable substance.

48. The method of paragraph 47, wherein the aseptic sealing is accomplished using a transparent membrane, which seals and protects the developing embryo, enabling it to hatch.

49. The method of paragraph 48, wherein the membrane is warmed near to its melting point to allow the membrane to bond to the egg shell.

50. The method of paragraph 49, wherein the warming is accomplished using a hot air gun, a flexible stamp filled with circulating hot fluid, a radiation source, an infrared source, or a laser.

51. The method of any of the proceeding paragraphs, wherein greater than 1,000 eggs are injected per hour.

52. The method of paragraph 51, wherein greater than 3,000 eggs are injected per hour.

Having thus described in detail embodiments of the present invention, it is to be understood that the invention defined by the appended claims is not to be limited to particular details set forth in the above description as many apparent variations thereof are possible without departing from the spirit or scope of the present invention.

What is claimed is:

1. An Embryonic Structure Targeting Injection System (ESTIS) for injecting a substance into a specific location within a developing avian embryo, or a specific location of an egg containing an avian embryo, comprising:
    a. a means for aseptically cutting the outer shell of an egg, such that a defined portion of the shell is prepared for subsequent removal;
    b. a means for removing the defined shell portion to produce an opening in the egg, wherein the means comprises a vacuum suction cup, a contact-less vacuum suction, or a mechanical arm;
    c. a means for mapping the x, y, z coordinates of embryonic structures to locate the specific injection location comprising a camera and a microprocessor;
    d. a means for injecting the substance into the specific injection location;
    e. a means for aseptically sealing the opening;
    f. an egg transfer assembly, which is capable of moving eggs from their incubation position, wherein the egg's stump pole is facing upward, to their injection position, wherein the egg's pointed pole is facing upward such that it is accessible to the injection needle; and
    g. an egg holder or tray having an egg immobilization means, which employs either vacuum or a suitable mechanical means to fix the position of the egg or plurality of eggs, and a light source, or plurality of light sources, which is a component of the mapping means.

2. The system of claim 1, wherein the holder or tray is disinfectable, bio-compatible, and compatible with standard hatchery trays.

3. The system of claim 1, further comprising a pressure application means, which serves to apply a positive pressure to the air cavity in the stump end of the egg to diminish embryo deepening after opening of the egg.

4. The system of claim 3, further comprising a cooling means for cooling the light source or plurality of light sources.

5. The system of claim 3, wherein the light source selected from white light and a specific color of light, wherein the specific color of light can optionally be produced using optical filters in combination with the white light source.

6. The system of claim 3, wherein a specific amount of fluid is configured to be injected into the specific location of the avian embryo, or the specific location of the egg containing the avian embryo, before 120 hours post-fertilization; and, wherein the egg is configured to be incubated until the chicken hatches.

7. The system of claim 3, wherein the means for cutting is a $CO_2$ laser, a high-power LED laser, or a mechanical cutting means.

8. The system of claim 7, wherein the mechanical cutting means is a diamond or carbide drill.

9. The system of claim 7, wherein the LED laser light is green (center wavelength 535 nm, range 520 nm-550 nm); blue (center wave length 450 nm, range 440 nm-470 nm); yellow (center wave length 590 nm, range 575 nm-610 nm); or NIR (center wave 1200 nm, range of 1000 nm-1400 nm).

10. The system of claim 7, wherein the specific injection location is a blood vessel or the heart.

11. The system of claim 10, wherein the specific injection location is the heart and the volume of the substance is about 5 µL.

12. A method for safely injecting a substance into a specific location of an avian embryo, or a specific location of the egg containing the avian embryo, comprising the steps of:
    a. opening a fertilized avian egg;
    b. injecting a substance into a specific location of the embryo or the egg containing the embryo; and
    c. aseptically sealing the opening in the egg shell using a membrane, which seals and protects the developing embryo, thereby safely injecting the substance into the specific location of the avian embryo or the egg; wherein the method is performed using the system of claim 1.

13. The method of claim 12, comprising the steps of:
    a. detecting the x and y coordinates for the embryo and its structures;
    b. detecting the z coordinate, which represents the distance between the cutting means and the egg shell surface;
    c. determining a desired target structure, defined by x and y coordinates, into which a substance will be injected;
    d. positioning an injection needle tip sufficiently close to the determined target to allow for injection into the desired target embryonic structure; and
    e. injecting the substance into the structure.

14. The method of claim 12, comprising the steps of:
    a. detecting and locating the embryo and its structures without physically disrupting the egg's shell by:
        i. detecting the x and y coordinates for the embryo and its structures;
        ii. detecting the z coordinate, which represents the distance between the opening means and the surface of the egg shell;
        iii. determining a desired target structure, defined by x, y, and z coordinates, into which a substance will be injected;

b. penetrating the egg shell such that a defined portion of said egg shell is capable of being removed by a subsequent removal step; and
c. removing the defined egg shell portion, leaving behind the opening in said egg shell;
d. positioning an injection needle tip sufficiently close to the determined target structure to allow for injection into the desired target structure; and
e. injecting the substance into the structure.

15. The method of claim 12, further comprising the step of rotating the egg, or plurality of eggs, from its incubation position, wherein the egg's stump pole is facing upward, to an injection position, wherein the egg's pointed pole is facing upward such that it is accessible to the injection needle.

16. The method of claim 15, wherein the rotation is accomplished using a vacuum cup assembly.

17. The method of claim 15, wherein the egg or plurality of eggs B is placed on the egg holder or tray, wherein the egg immobilization means employs vacuum to fix the position of the egg or plurality of eggs.

18. The method of claim 17, further comprising applying a positive pressure to the air cavity in the stump end of the egg to avoid embryo deepening after opening of the egg.

19. The method of claim 18, wherein the light is shone through the egg, from stump end to pointed end, to a detector unit, which is a component of the mapping means, such that the detection unit is positioned on the opposite side of the egg, relative to the light source.

20. The method of claim 19, wherein the detection unit is an area sensor (CMOS or CCD).

21. The method of claim 20, wherein the detection unit is made of silicon or a NIR sensitive material.

22. The method of claim 21, wherein the NIR-sensitive material is indium gallium arsenite.

23. The method of claim 20, wherein the detection unit comprises optics including a tunable lens to adjust the focus of the optics to the egg surface.

* * * * *